US006455578B1

(12) United States Patent
Di Napoli

(10) Patent No.: US 6,455,578 B1
(45) Date of Patent: Sep. 24, 2002

(54) AROMATIC DERIVATIVES AND IRON COMPLEXES THEREOF FOR THE USE AS NORMALIZING AGENTS OF THE IRON LEVEL

(75) Inventor: Guido Di Napoli, Collonge-Bellerive (CH)

(73) Assignee: Laboratoire Medidom S.A., Geneva (CH)

( * ) Notice: Subject to any disclaimer, the term of this patent is extended or adjusted under 35 U.S.C. 154(b) by 0 days.

(21) Appl. No.: 09/830,800

(22) PCT Filed: Oct. 29, 1999

(86) PCT No.: PCT/EP99/08222

§ 371 (c)(1),
(2), (4) Date: Apr. 30, 2001

(87) PCT Pub. No.: WO00/26205

PCT Pub. Date: May 11, 2000

(30) Foreign Application Priority Data

Nov. 2, 1998 (IT) .......................................... MI98A2350

(51) Int. Cl.$^7$ ........................ A01N 43/16; A01N 35/00; A61K 31/185; C07D 319/00; C07C 49/76
(52) U.S. Cl. ...................... 514/456; 514/457; 514/460; 514/577; 514/681; 514/688; 514/690; 549/398; 549/399; 549/403; 568/335; 568/336; 568/337
(58) Field of Search .................................. 568/335, 336, 568/337; 549/398, 399, 403; 514/456, 457, 460, 577, 681, 688, 689, 690

(56) References Cited

U.S. PATENT DOCUMENTS 4,122,200 A * 10/1978 Briet et al.
4,281,008 A * 7/1981 Chamberlain et al.
5,071,898 A * 12/1991 Wirth et al.

OTHER PUBLICATIONS

Klopman et al., "Computer–Automated Structure Elevation of Flavonoids and Other Structurally Related Compounds as Glyoxalase I Enzyme Inhibitors", *Molecular Pharmacology*, 34:218–222. (1988).
Cadenas, "Biochemistry of Oxygen Toxicity", *Annu. Rev. Biochem.* 58:79–110, (1989).
Rothman et al., "Cellular Pool of Transient Ferric Iron, Chelatable by Deferoxamine and Distinct from Ferritin, that is Involved in Oxidative Cell Injury", *Molecular Pharmacology*, 42: 703–710. (1992).
Minotti, et al. "Secondary Alcohol Metabolites Mediate Iron Delocalization in Cytosolic Fractions of Myocardial Biopsies Exposed to Anticancer Anthracyclines", *J. Clin. Invest.*, 95: 1595–1605. (1995).
Boelaert, et al., "Altered Iron Metabolism in HIV Infection: Mechanisms, Possible Consequences, and Proposals for Management", *Infectious Agents and Disease*, 5: 36–46, 1996.

Gupta et al., "Role of Iron and Iron Chelation Therapy in Oxygen Free Radical Mediated Tissue Injury in an Ascending Mouse Model of Chronic Pyelonephritis", *Comp. Immun. Microbial Infect. Dis.* vol. 20, No. 4, pp. 299–307 (1997).
Lisa Lih–Brody et al., "Increased Oxidative Stress and Decreased Antioxidant Defenses in Mucosa of Inflammatory Bowel Disease", *Digestive Diseases and Sciences*, vol. 41, No. 10, pp. 2078–2086 (Oct. 1996).
Tomi–Pekka Tuomainen et al., "Association Between Body Iron Stores and the Risk of Acute Myocardial Infarction in Men", *Circulation*, (1998:)97: 1461–1466.
Gassen et al., "The Potential Role of Iron Chelators in the Treatment of Parkinson's Disease and Related Neurological Disorders", *Pharmacology and Toxicology*, 80, 159–166 (1997).
Chiara–Corti, "Serum Iron Level, Coronary Artery Disease, and All–Cause Mortality in Older Men and Women", *Am J. Cardiol.*, 120–127, 1997.
Matthews et al., "Iron and Atherosclerosis: Inhibition by the Iron Chelator Deferiprone (L1)", *Journal of Surgical Research* 73, 35–40 (1997).
Olivieri et al., "Long–Term Safety and Effectiveness of Iron–Chelation Therapy with Deferiprone for Thalassemia Major", The New Engl. J. of Med. vol. 339, No. 7, pp. 417–423. (1998).

* cited by examiner

*Primary Examiner*—Johann Richter
*Assistant Examiner*—Sikarl A. Witherspoon
(74) *Attorney, Agent, or Firm*—Abelman, Frayne & Schwab

(57) ABSTRACT

The present invention is directed to aromatic derivatives of formula (I), wherein: $R_1$ is (a), wherein $R_3$ and $R_4$ are selected from between H and OH, provided that $R_3$ and $R_4$ are not simultaneously H, and $R_2$ is H; or $R_1$ and $R_2$ taken together, are (b), wherein $R_5$ is selected from between $CH_3$ and $(CH_2)_5OH$, to the iron complexes thereof, and to their use for the preparation of pharmaceutical compositions for the normalization of iron level.

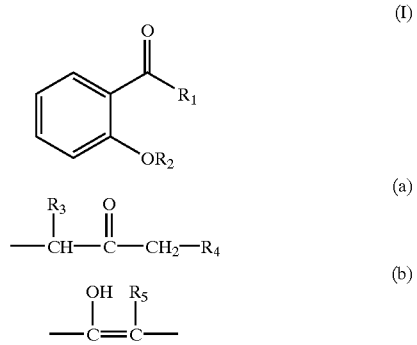

12 Claims, No Drawings

AROMATIC DERIVATIVES AND IRON COMPLEXES THEREOF FOR THE USE AS NORMALIZING AGENTS OF THE IRON LEVEL

This application is the National Stage of International Application No. PCT/EP99/08222, filed on Oct. 29, 1999.

FIELD OF THE INVENTION

The present invention relates to aromatic derivatives of formula (I) hereinafter reported and to iron complexes thereof, for the preparation of pharmaceutical compositions useful as normalising agents of the iron level.

STATE OF THE ART

Iron overload in the body, due to major defects in iron metabolism, such as genetic hemochromatosis and thalassemia, or due to minor causes, such as for example transfusions for hemolytic anemia, can bring the physiological defense reaction to saturation, thus having a toxic effect.

Such an effect is due to the expansion of the "Free Iron Pool", which induces the production of oxygen active species responsible for the inactivation of cellular enzymes, for modifications in the membrane lipids, for DNA alterations, etc. (E. Cadenas, *Ann. Rev. Biochem.*, 1989, 58: 79–110).

Therefore the consequences of the "Free Iron Pool" expansion can range from genotoxicity of the metal which causes the develop of tumours, to various organ pathologies, such as cirrhosis, diabetes, cardiopathy, hypogonadism and arthropathy.

Even in absence of an increase of the total iron in the body, an expansion of "Free Iron Pool" may happen, in association with many pathologic conditions, as for example neurodegenerative pathologies (M. Gassen et al., *Pharmacol. Toxicol.*, 1997, 80(4): 159–166), atherosclerosis (A. J. Matthews et al., *J. Surg. Res.*, 1997, 73(1): 35–40), ischaemic cardiopathy (T. P. Tuomainen et al., *Circulation*, 1998, 97(15): 1461–1466), chronic diseases of intestine (R. A. Floyd et al., *Dig. Dis. Sci.*, October 1996, 41(10): 2078–86), and may cause the beginning or the development of the pathobiological event.

A strict correlation between alterations in the iron methabolism and HIV infections (J. R. Boelaert et al., *Infect. Agents Dis.*, January 1996, 5(1): 36–46), as well as a connection between cardiotoxicity induced by iron and methabolism of antineoplastic agents in persons subjected to antitumoural therapy (G. Minotti et al., *J. Clin. Invest.*, April 1995, 95(4): 1595–605), has been recently observed.

Moreover, it has been proved that the presence of "Free Iron" has a predominant role in the reactions bearing to the formation of free radicals and to the propagation of the damages due to free radicals, to which are associated for example inflammatory pathologies, such as arthritis and pyelonephritis (R. Gupta et al., *Comp. Immunol. Microbiol. Infect. Dis.*, 1997, 20(4): 299–307), and senescence (M. C. Corti et al., *Am. J. Cardiol.*, 1997, 79(2): 120–127).

At present, it is known the use of iron chelating agents in the treatment of systemic iron overload, associated to pathologies such as thalassemia or hemochromatosis.

The compounds used in such treatments show several drawbacks. For example, desferrioxamine, one of the substances more frequently used in this type of treatments, besides iron it binds many other important metals, such as aluminum, it is a very expensive product, it cannot be administered by oral route, and it has a half-life so short that continuous administration by subdermal infusion is necessary (R. J. Rothman et al., *Mol. Pharmacol.*, 1992, 42: 703–710).

Other medicaments are known containing complexing agents of iron, such as deferiprone and derivatives thereof, showing a great bioavailability, but also a high toxicity caused just by their bioavailability, which bring for example to the onset of agranulocythemia, epathic fibrosis, etc. (N. F. Olivieri et al., *N. Engl. J. Med.*, 1998, 339(7): 417–423).

Moreover, the medicaments, used up to now, have a dramatic effect on the cellular methabolism of iron, on which they produce a deep unbalance: as a matter of fact, they recall a great quantity of metal from the deposits of the organism and therefore they can be administered neither in the precox phases nor for sake of prophilaxys during hemochromatosis or thalassemia, nor in conditions in which the expansion of "Free Iron Pool" should be contrasted avoiding a variation in the quantity of the functional iron or of the iron stored in deposits.

It is therefore deeply felt the need of new compounds suitable for preparing pharmaceutical compositions, able to act as chelating agents of the total iron as well as of the "Free Iron Pool", by removing it from cells and eliminating the resulting complex in urine.

It is felt as much the need of new pharmaceutical compositions for the treatment of pathologies to which a lack of iron in the body is associated.

SUMMARY OF THE INVENTION

Now the Applicant has surprisingly found that aromatic derivatives of formula (I):

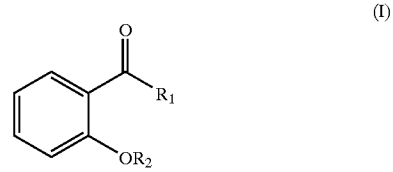

wherein:

$R_1$ is

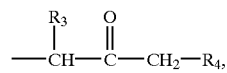

wherein $R_3$ and $R_4$ are selected from between H and OH, provided that $R_3$ and $R_4$ are not simultaneously H, and $R_2$ is H; or $R_1$ and $R_2$, taken together, are

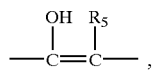

wherein $R_5$ is selected from between $CH_3$ and $(CH_2)_5OH$, are able to bind stably the iron, in particular Fe(III).

Said compounds of formula (I) are suitable for the preparation of pharmaceutical compositions for oral administration, and show a high absorption and a high ability to permeate the biological membranes, in the form of free ligands as well as in the form of iron complexes.

Said pharmaceutical compositions are therefore useful for the treatment of all the pathological conditions related to an iron overload, in the case of an increase of the total iron as well as in the case of a relative increase in the iron level due to the expansion of the "Free Iron Pool".

The iron complexes of the formula (I) compounds are also useful for the preparation of pharmaceutical compositions to be used in the treatment of pathologies related to a deficiency of iron, in the acute phase as well as for the chronic pathology.

It is therefore one object of the present invention the compounds of formula (I) for the preparation of pharmaceutical compositions for the use, in particular, as iron chelating agents, and the complexes thereof useful as iron release agents for hypoferremia.

Further object of the present invention are the compounds of formula (I) wherein $R_1$ is

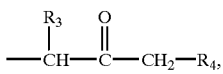

wherein $R_3$ is OH and $R_4$ is H, OH, and $R_2$ is H; or $R_1$ and $R_2$, taken together, are

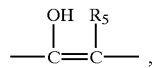

wherein $R_5$ is $(CH_2)_5OH$.

Features and advantages of compounds of formula (I) as iron chelating agents and of the iron complexes thereof according to the present invention will be illustrated in detail in the following description.

DETAILED DESCRIPTION OF THE INVENTION

The present invention relates to compounds having the formula (I) above reported for the preparation of pharmaceutical compounds, in particular of pharmaceutical compounds for the use as iron chelating agents. The iron complexes of the present formula (I) compounds have therapeutic application too, as agents for the iron release.

The present formula (I) compounds, which can be easily prepared according to processes known in the art, show a high affinity for iron, in particular for Fe(III), giving stable complexes of such metal presenting different metal/ligand ratios. Concerning the preparation of said complexes, they are tipically prepared by reacting a compound of formula (I) with Fe(III) ions deriving from a ferric salt selected from the group consisting of inorganic salts of Fe(III), preferably perchlorate, chloride and sulphate, and more preferably perchlorate.

Said reaction is carried out in a solvent selected from the group consisting of acetone, chloroform, dichloromethane and aqueous solutions containing from 5 to 10% of dimethylsulphoxide, preferably in acetone.

Chelation experiments of iron have been carried out with the present formula (I) compounds wherein $R_1$ and $R_2$, taken together, are

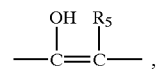

wherein $R_5$ is selected from between $CH_3$ and $(CH_2)_5OH$, and it has been found that they form a Fe(III) complex having a molar ratio ligand:metal equal to 2:1.

The preparation of said complex is preferably carried out at room temperature by reacting a compound of formula (I) with ferric perchlorate in acetone.

The stability constant of the Fe (III) complex with the compound of formula (I) wherein $R_1$ and $R_2$, taken together, are

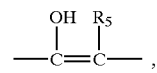

wherein $R_5$ is $CH_3$, has been measured by voltammetry with a Pt electrode as the working electrode and with a calomel electrode as the reference electrode, obtaining a stability constant equal to $3.0 \times 10^{10}$.

Analogous chelation experiments and measurements of the stability constants of the present complexes have been carried out for the other formula (I) compounds, obtaining analogous results.

The ability of the present formula (I) compounds and of iron complexes thereof for permeating the biologic membranes has been investigated by partition tests between n-ottanol and an aqueous solution of said compounds, which showed their greater affinity for the organic solvent.

In particular, partition experiments have been carried out between n-ottanol and an aqueous solution 20 mM of tris(hydroxymethyl)aminomethane chlorohydrate brought to pH=7.4 by adding sodium phosphate, obtaining values of the ripartition coefficient, expressed as the ratio between the concentration of the compound in the organic phase and that in the aqueous phase, tipically higher than 20, for the present formula (I) compounds as well as for the Fe (III) complexes thereof.

The compounds of formula (I) and iron complexes thereof according to the present invention can be formulated with pharmaceutically acceptable excipients and/or diluents, with the aim of preparing pharmaceutical compositions for the treatment of pathologies characterised by an overload or respectively by a lack of iron in the body.

For example, dimethylsulphoxide can be used as the diluent, and examples of excipients of possible use are methylcellulose, β-cyclodextrins and polyethyleneglycol.

The concentration of the present formula (I) compound or that of the corresponding iron complexes in the pharmaceutical compositions ranges between 0.4 and 0.8% by weight with respect to the total weight of the composition.

Said compositions comprising the formula (I) compounds are efficient as iron chelating agents in the treatment of the systemic ironoverload, such as in the case of thalassemia and hemochromatosis, as well as in the treatment of the expansion of the "Free Iron Pool".

The pharmaceutical compositions comprising the formula (I) compounds according to the present invention are therefore useful in the treatment of several pathologies to which an iron overload in the body is associated, comprising hemochromatosis, thalassemia, anemia associated to iron overload and conditions associated to secondary siderosis, neurodegenerative pathologies, such as Parkinson's disease and Alzheimer's disease, ischaemic cardiopathy, inflammatory chronic pathologies, such as arthritis, pyelonephritis, and inflammatory chronic diseases of the intestine, alterations in the metabolism of iron associated to HIV infections, cardiotoxicity due to doxorubicin and anthracyclines, atherosclerosis and senescence.

The pharmaceutical compositions comprising the iron complexes of the present formula (I) compounds are useful in the treatment of the pathologies to which a lack of iron in the body is associated, comprising sideropenic anemia in the acute phase as well as in the chronic form.

The following examples are given to provide non-limiting illustrations of the present invention.

EXAMPLE 1

Preparation of 3-hydroxy-2-methyl-4H-1-benzopyran-4-one (Compound of formula (I) wherein $R_1$ and $R_2$, taken together, are

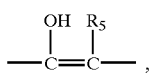

wherein $R_5$ is $CH_3$)

2-hydroxyacetophenone (20 g) is dissolved in ethyl acetate (200 ml). Sodium powder (16 g) is gradually added in 15–20 minutes, so to maintain a reasonable reflux. The mixture is refluxed for 1 hour, then it is allowed to cool. Grinded ice (200 g) is then added until precipitation of sodium acetylacetophenone, which is then isolated by filtration under vacuum. The solid product is then crystallised with acetic acid 40% (200 ml), obtaining acetyl acetophenone (19.6 g) as pulverulent crystals (m.p.=95° C.; yield= 75%).

Concentrated sulphuric acid (30 g) is added to acetyl acetophenone (15 g) obtained as above described. After cooling at room temperature, water is added until precipitation of a white powder, which is isolated by filtration under vacuum and washed with cold water. 2-methyl-4H-1-benzopyran-4-one (10 g) is obtained (m.p.=71° C.; yield= 74%).

Pd on $CaCO_3$ (1.6 g) is suspended in benzene (15 ml) in a suitable hydrogenation flask. The activation of the catalysator occurs by absorption of $H_2$ at room temperature, then 2-methyl-4H-1-benzopyran-4-one (1.6 g) dissolved in benzene (15 ml) is added. The catalysator is allowed to absorb ca. 200 ml of $H_2$ at room temperature and pressure. After filtration, benzene is evaporated obtaining a pale yellow oleous liquid, to which a little volume of the mixture petroleum ether:ethylic ether 1:1 is added. The obtained solution is purified by chromatography with a silica gel column (600–200 mesh) with the above mixture as the eluent. 0.9 g of the purified and dried product are obtained (yield=60%); said product is a colourless oil which is resulted 2,3-dihydro-2-methyl-4H-1-benzopyran-4-one.

2,3-dihydro-2-methyl-4H-1-benzopyran-4-one (1.62 g) is dissolved in ethanol 95% (50 ml) and the solution is refluxed under stirring. In 10–15 minutes isoamylnitrite (8 ml) and concentrated HCl (40 ml) are added drop by drop. Heating and stirring are stopped, and the resulting mixture is allowed to stand ca. 2 hours. Then water (200 ml) is added until precipitation of a white solid. The solvent is evaporated, obtaining a solid product which is dissolved in a little volume of chloroform and purified on silica gel in equilibrium with the same solvent. The purified product contains a low percentage of yellow impurities which can be completely eliminated by crystallisation in acetone. The residual solvent is then eliminated, obtaining 0.97 g of 3-hydroxy-2-methyl-4H-1-benzopyran-4-one (colourless crystals; m.p.=179–180° C.; IR: 1632, 1666 e 3301 $cm^{-1}$; yield= 51%).

EXAMPLE 2

Preparation of 3-hydroxy-2-(5-hydroxypenthyl)-4H-1-benzopyran-4-one (Compound of formula (I) wherein $R_1$ and $R_2$, taken together, are

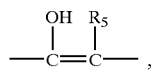

wherein $R_5$ is $(CH_2)_5OH$)

2-hydroxyacetophenone (13.6 g) and toluene (200 ml) are introduced in a reactor. Granulated sodium (4.4 g) is gradually added under stirring so to maintain a moderate reflux. Once the reaction is finished, ethyl 6-hydroxyesanoate (28 g) is added, and the mixture is allowed to react under stirring and under a moderate reflux for 2 hours; the product formation is controlled by TLC with the mixture diethyl ether:petroleum ether 9:1. After cooling, filtration under vacuum is carried out and the solid product is then washed with diethyl ether.

The solid product is then redissolved in acetic acid 40% (100 ml), and to the so obtained solution $NaHCO_3$ is gradually added until neutrality. The solution is then poured in a separatory funnel and three extractions with diethyl ether are made (each with 100 ml of the solvent). The ethereal phases from each extraction are collected together and dried by addition of anhydrous $Na_2SO_4$: after the drying agent's addition the suspension is stirred for 5 minutes, then filtered; the solvent is evaporated, obtaining an oil which is purified by chromatography with a silica gel column and the mixture diethyl ether:petroleum ether 9:1 as the eluent. 1-(2-hydroxyphenyl)-1,3-[3-(5-hydroxypentyl)]butandione (8 g) is obtained.

96% $H_2SO_4$ (16 g) are added to the obtained product (8 g) and the mixture is caused to react under stirring for few minutes. After cooling at room temperature, water is added, then $NaHCO_3$ is gradually added in order to neutralise sulphuric acid. Three extractions with diethyl ether (150 ml) are carried out. The three resulting ethereal phases are collected and dried by addition of anhydrous $Na_2SO_4$. After filtration and evaporation of the solvent an oil is obtained which is then purified by chromatography with a silica gel column and the mixture ethylic ether:acetone 80:20 as the eluent. 0.74 g of 2-(5-hydroxypentyl)-4H-1-benzopyran-4-one are obtained.

Pd on $CaCO_3$ (0.74 g) are suspended with benzene in a suitable hydrogenation flask; the catalysator is allowed to absorb $H_2$ at room pression and temperature. Once the catalysator stops to absorb $H_2$, 2-(5hydroxypentyl)-4H-1-benzopyran-4-one (0.74 g) dissolved in benzene is added, and hydrogenation is carried out: ca. 100 ml of $H_2$ at room pression and temperature are absorbed. After ca. 24 hours a filtration is carried out, and benzene is evaporated obtaining an oil to which a small volume of diethyl ether is added. The purification of this product is carried out by chromatography with a silica gel column and diethyl ether as the eluent. 2,3-dihydro-2-(5-hydroxypentyl)-4H-1-benzopyran-4-one (0.23 g) is obtained.

2,3-dihydro-2-(5-hydroxypentyl)-4H-1-benzopyran-4-one (0.23 g) is dissolved in ethanol 95% (5 ml), and the solution is refluxed under stirring. HCl (6.2 ml) and isoamylnitrite (1.2 ml) are then added drop by drop. Stirring and heating are then stopped and the reaction mixture is allowed to stand for ca. 1 hour. The solvent is evaporated, water is then added and the product extracted with diethyl ether. The ethereal phase is dried by addition of anhydrous $Na_2SO_4$. After filtration and evaporation of the solvent an oil is obtained which is purified by chromatography with silica gel column and the mixture diethyl ether:methanol 98:2 as the eluent. 3-hydroxy-2-(5-hydroxypentyl)-4H-1-benzopyran-4-one (99.2 mg) is obtained. By crystallisation in cycloesane or diethyl ether the product in crystalline form is obtained (m.p.=111–112° C.).

EXAMPLE 3

Preparation of 3-hydroxy-2-(5-hydroxypentyl)-4H-1-benzopyran-4-one (Compound of formula (I) wherein $R_1$ and $R_2$, taken together, are

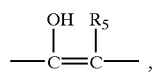

wherein $R_5$ is $(CH_2)_5OH$)

Ethyl 6-hydroxyesanoate (100 mmol) is dissolved under stirring in 3,4-dihydropyrane (120 mmol); p-toluenesulphonic acid (15 mg) is then added and the mixture is allowed to react at room temperature for ca. 1 hour. The end of the reaction is verified by TLC on silica gel and the mixture petroleum ether:diethyl ether 1:1 as the eluent by using iodium vapors as revelator. When the reaction has finished, an aqueous solution, basic by addition of sodium carbonate, is added and accurately stirred. The product, obtained with quantitative yield, is extracted with diethyl ether.

Toluene (15 ml), previously distillated on sodium, is poured on granulated sodium (300 mmol) and heated to reflux. When the reflux is reached, the heating is stopped, and ethyl 6-hydroxyesanoate (200 mmol) obtained as above described, with the hydroxylic group still protected, is added drop by drop in 90–120 minutes together with 2-hydroxyacetophenone (100 mmol) in toluene (15 ml). The mixture is allowed to react for 4–5 hours, controlling the end of reaction by TLC on silica gel with the mixture petroleum ether:diethyl ether 1:1 as the eluent.

At the reaction's end ethanol is added so to eliminate the excess of sodium, then acetic acid 7.5% (100 ml) is added, controlling that pH is ca. 10.

The condensation product with the hydroxylic group still protected is extracted by carrying out three extractions with diethyl ether and two extractions with ethyl acetate, finally obtaining the product with a 60% yield.

The so obtained product, dissolved in acetic acid (2 ml), is put into a reactor, which is immersed in an oil bath, so to bring the temperature to 130° C., and maintain it for ca. 1 hour. At first the distillation of the azeotrope water/acetic acid occurs, then a vacuum pump is applied in order to promote the distillation of the remaining acetic acid.

The cyclisation is verified by TLC on silica gel with diethyl ether as the eluent. At the end of cyclisation a mixture acetic acid:water 4:1 (50 ml) is added and the temperature is brought to 50° C. The reaction mixture is maintained under stirring at 50° C. until the protection group is completely removed, obtaining 2-(5-hydroxypentyl)-benzopyran-4-one. The formation of this product is verified by TLC on silica gel with diethyl ether containing 2% of methanol as the eluent.

The obtained product is extracted with diethyl ether after the addition of water, then the solvent is evaporated and the product is purified by column chromatography with diethyl ether containing 2% of methanol as the eluent, thus obtaining pure 2-(5-hydroxypentyl)-4H-1-benzopyran-4-one with a 50% yield.

Pd 5% on calcium carbonate (1 g) is put in ethanol (20 ml) and hydrogenated. When the catalysator does not absorb $H_2$ anymore, a solution prepared by dissolving in ethanol (40 ml) 2-(5-hydroxypentyl)-4H-1-benzopyran-4-one (4 g), obtained as described above, is added, and hydrogenation is carried out. The mixture is caused to react for 4–5 hours, then filtered; the reaction product is essiccated and redissolved in the minimum quantity of diethyl ether for the purification by chromatography on a silica column with diethyl ether as the eluent. 2,3-dihydro-2-(5-hydroxypentyl)-4H-1-benzopyran-4-one is thus obtained with 50% yield.

The so obtained product (1 mmol) is dissolved in ethanol 95% (5 ml), and the solution is refluxed under stirring. HCl (6.5 ml) and isoamylnitrite (1.2 ml) are added drop by drop to this solution. Then heating and stirring are stopped, and the reaction mixture is allowed to stand for 1 hour. The solvent is evaporated, water is added, making then an extraction with diethyl ether; the ethereal phase is dried by addition of anhydrous $Na_2SO_4$. By filtration and avaporation of the solvent 3-hydroxy-2-(5-hydroxypentyl)-4H-1-benzopyran-4-one is obtained with 25% yield. This product is then purified by chromatography on silica column with the mixture diethyl ether:methanol 98:2 as the eluent, thus obtaining pure 3-hydroxy-2-(5-hydroxypentyl)-4H-1-benzopyran-4-one (fluorescent under a light with $\lambda$=360 nm;

$^1$H-NMR (CDCl$_3$, 200 MHz) δ from 1.5 to 1.88 ppm (multiplet), 2.5 ppm (triplet), 3.6 ppm (triplet), from 7.35 to 8.25 ppm (aromatic H); MS m/e 248 M$^+$).

EXAMPLE 4

Preparation of the Fe(III) complex of 3-hydroxy-2-methyl-4H-1-benzopyran-4-one 3-hydroxy-2-methyl-4H-1-benzopyran-4-one (7 mg; 0.04 mmol), prepared as described in Example 1, is dissolved in acetone (5 ml); to this solution ferric perchlorate (7 mg; 0.02 mmol) is added at room temperature, thus obtaining the quantitative formation of the complex chelating agent:Fe (III) 2:1. By evaporation of acetone the complex is isolated as a dark red pulverulent residue, characterised by mass spectroscopy.

The complexation cynetics has been moreover studied by cyclic voltammetry with a Pt electrode as the working electrode and a calomel electrode as the reference electrode, in the following conditions:ferric perchlorate (7 mg) is dissolved in 20 ml of a NaCl solution 150 mM containing 5% of DMSO, and this solution is put into the voltammetric cell for the plot registration; from this plot the half-wave potential for the ferric salt can be deduced: $(E_{1/2})s$ $Fe^{3+}/Fe^{2+}$=0.420 V.

3-hydroxy-2-methyl-4H-1-benzopyran-4-one (10.5 mg) is dissolved in DMSO (3 ml), and with the so obtained solution 4 additions are made to the voltammetric cell, registering the cyclic voltammetric plot after every addition. After the first addition of 0.5 ml the plot is registered, from which the half-wave potential of the complex is obtained: $(E_{1/2})s$ $Fe^{3+}/Fe^{2+}$=0.120 V. Successively 0.5 ml (second addition), 1 ml (third addition), 1 ml (fourth addition) of the solution of the chelating agent in DMSO are then added. After the third addition the oxidation wave $Fe^{3+}/Fe^{2+}$ is disappeared, thus proving that free iron is not in the solution after the molar ratio chelating agent:metal 2:1 is reached.

The stability constant of the complex is calculated according to the following formula:

$$(E_{1/2})s - (E_{1/2})c = \frac{0.059}{n}\log\beta + \frac{0.059}{n}p\log c$$

wherein $(E_{1/2})s$ e $(E_{1/2})c$ are the half-wave potential of the salt and, respectively, of the complex above reported, n is the number of electrons, $\beta$ is the stability constant of the complex and c is its concentration, and p is the number of chelating agent molecules in the complex. The so calculated value of the stability constant is $3.0 \times 10_{10}$.

EXAMPLE 5

Preparation of the Fe(III) complex of 3-hydroxy-2-(5-hydroxypentyl)-4H-1-benzopyran-4-one According to a procedure similar to that described in Example 4, the Fe(III) complex of the 3-hydroxy-2-(5-hydroxypentyl)-4H-1-benzopyran-4-one obtained as in Example 3, is prepared (MS m/e 549 $M^+$). This indicates the formation of a neutral complex having a ratio chelating agent:Fe(III) 2:1, in which three of the four oxydrylic groups of chelating agent are deprotonated in the complex.

EXAMPLE 6

Partition test on 3-hydroxy-2-methyl-4H-1-benzopyran-4-one and on the iron complex thereof The partition coefficient between n-octanol and an aqueous solution 20 mM of tris(hydroxymethyl)aminomethane brought to pH=7.4 by the addition of sodium phosphate has been determined by spectrophotometry at room temperature for 3-hydroxy-2-methyl-4H-1-benzopyran-4-one and for the related Fe(III) complex.

In the aqueous solution the 3-hydroxy-2-methyl-4H-1-benzopyran-4one obtained as described in Example 1 was dissolved in the quantity sufficient to have a concentration equal to $10^{-4}$ M. 5 ml of said solution were centrifuged with 5 ml of n-octanol, and the two resulting phases were separated for a concentration determination on each by spectrophotometry.

The partition coefficient, expressed as the ratio between the concentration of the compound in n-octanol and its concentration in the aqueous solution, resulted 24. In the same aqueous solution above described the Fe(III) complex obtained as in Example 4 was dissolved, in the sufficient quantity to obtain a concentration equal to $2\times10^{-4}$ M. 5 ml of said solution are centrifuged with 5 ml of n-octanol, then the two resulting phases were separated for a concentration determination on each by spectrophotometry. A partition coefficient equal to 25 was obtained.

EXAMPLE 7

Partition data on 3-hydroxy-2-(5-hydroxypentyl)-4H-1-benzopyran-4-one and on the related iron complex According to the procedure described in Example 6 partition data were determined between n-octanol and an aqueous solution 20 mM of tris(hydroxymethyl) aminomethane chlorhydrate brought to pH 7.4 by addition of sodium phosphate, for 3-hydroxy-2-(5-hydroxypentyl)-4H-1-benzopyran-4-one prepared as in Example 3 as well as for the related Fe(III) complex prepared as in Example 5.

In the aqueous solution 3-hydroxy-2-(5-hydroxypentyl)-4H-1-benzopyran-4-one as prepared in Example 3 was dissolved so to obtain a concentration equal to 100 mM. 5 ml of said solution were centrifuged with 5 ml of n-octanol, then the two resulting phases, the aqueous and the organic one, were separated for a concentration determination on each by spectrophotometry.

The same experiment was repeated by dissolving the Fe(III) complex prepared as in Example 5 in the above described aqueous solution.

In both cases the compound completely pass in the alcoholic phase.

EXAMPLE 8

In vitro tests on permeation into erythrocytes of 3-hydroxy-2-methyl-4H-1-benzopyran-4-one and of the related Fe(III) complex Solutions of 3-hydroxy-2-methyl-4H-1-benzopyran-4-one prepared as in Example 1 and the related Fe(III) complex obtained in acetone as in Example 4 were used for suitable sampling in incubation flasks. For the complex acetone is evaporated, and the biologic samples are then added to the residue. Whole blood of rat deprived of leucocytes, or alternatively erythrocytes washed and resuspended in 127 mM of sodium phosphate 50% buffer (pH=7.4) and containing 23 mM of NaCl, were added into the incubation flasks and incubated at 37° C. for 15 and respectively 30 minutes.

At those times erythrocytes were separated by centrifugation and separately extracted together with the supernatants with 2 volumes of ethyl acetate. The related quantities of the tested substances were measured by spectrophotometry in ethyl acetate and compared with suitable standards. After 30 minutes of incubation the 3-hydroxy-2-methyl-4H-1-benzopyran-4-one as well as the related Fe(III) complex were found in the erythrocytes for 51% and for 49% in the aqueous medium. After 30 minutes of incubation 50% of the sedimented erythrocytes are resuspended in their fresh plasma and the remaining 50% in fresh buffer.

After a further 30 minutes incubation at 37° C. the 3-hydroxy-2-methyl-4H-1-benzopyran-4-one as well as the related iron complex were equally distributed in the erythrocytes, previously overloaded, and in the aqueous medium in which they were resuspended, thus proving that such compounds are distributed in a practically uniform way in the intracellular and in the extracellular environment, and a balance is reached in ca. 30 minutes as far as erythrocytes are concerned.

EXAMPLE 9

In vitro tests on permeation into erythrocytes of 3-hydroxy-2-(5-hydroxypentyl)-4H-1-benzopyran-4-one and of the related Fe(III) complex Erhytrocytes of rat were separated from their plasma deprived of leucocytes. Part of the erythrocytes were resuspended in sodium phosphate 50% buffer (pH=7.4), and another part of the erythrocytes were joined to part of their plasma so to obtained a 50% hematocrit. To both suspensions were added alternatively 100 mg/l of 3-hydroxy-2-(5-hydroxypentyl)-4H-benzopyran-4-one prepared as in Example 3 and 50 mg/l of the related Fe(III) complex prepared as in Example 5, and the incubation was made at 37° C. After 30 minutes the erythrocytes were separated by centrifugation and extracted separately together with supernatants with ethyl acetate. The quantities of the tested substances were measured by spectrophotometry in ethyl acetate and compared to suitable standards.

After 30 minutes incubation the 40% of 3-hydroxy-2-(5-hydroxypenthyl)-4H-1-benzopyran-4-one, as well as of the ferric complex thereof, were found in the erythrocytes and the remaining 60% in the medium represented by plasma. When the medium is the phosphate buffer the 60% of the tested compounds were found in erythrocytes and the remaining 40% in the medium.

After sedimentation 50% of the erythrocytes containing the tested compounds was resuspended in their plasma and the remaining 50% in fresh buffer. After a further 30 minutes incubation at 37° C. 60% of 3-hydroxy-2-(5-hydroxypentyl)-4H-1-benzopyran-4-one and of the related complex were found in the plasmatic medium and the remaining 40% in the aqueous medium containing the phosphate buffer. Therefore the chelating agent as well as the related ferric complex do permeate into cellular membranes in both directions, and are uniformly distributed in the intracellular and in the extracellular environment.

EXAMPLE 10

In vivo tests on permeation of rat erythrocytes by 3-hydroxy-2-methyl-4H-1-benzopyran-4-one The tests are performed on male rats Sprague-Dawley weighting from 250 to 300 g.

The chelating agent 3-hydroxy-2-methyl-4H-1-benzopyran-4-one prepared as in Example 1, vehiculated by 4 parts of β-cyclodextrine for each part of chelating agent, is administered to the rats in a single oral dose comprising 20 mg of chelating agent per Kg of body weight. At regular time intervals, after ½ hour, 1 hour, 4 hours, 24 hours e 48 hours starting from administration, the presence of the chelating agent in the rats is evaluated by spectrophotometry and by fluorimetry: 3-hydroxy-2-methyl-4H-1-benzopyran-4-one is found already in the first hour in erythrocytes, in brain and liver showing a maximum in the fourth hour, and in urine starting from twentyfourth hour.

EXAMPLE 11

In vivo tests on permeation of rat erythrocytes by 3-hydroxy-2-(5-hydroxypentyl)-4H-1-benzopyran-4-one The tests are performed on male rats Sprague-Dawley weighting from 250 to 300 g.

The chelating agent 3-hydroxy-2-(5-hydroxypentyl)-4H-1-benzopyran-4-one prepared as in Example 3 is administered to the rats in a single oral dose, comprising 2% of methyl cellulose and 20 mg of chelating agent per Kg of body weight. The presence of 3-hydroxy-2-(5-hydroxypentyl)-4H-1-benzopyran-4-one has been revealed in urine after 12 hours, 24 hours and 48 hours from administration. When 20 mg of 3-hydroxy-2-(5-hydroxypentyl)-4H-1-benzopyran-4-one per Kg of body weight are administered in DMSO by intraperitoneal route, its presence in plasma and erythrocytes has been revealed after 15, 30 e 60 minutes after the treatment.

TABLE 1

Qualitative detection of 3-hydroxy-2-methyl-4H-1-benzopyran-4-one in rat tissues and its excretion.

| Time after administration | Plasma | Erythrocytes | Liver | Brain | Urine | Faeces |
|---|---|---|---|---|---|---|
| 1/2 hr | p(+) | p(+) | A | a | a | a |
| 1 hr | p(++) | p(+) | p(+) | p(+) | a | a |
| 4 hr | p(++) | p(+++) | p(+++) | p(++) | p(+) | a |

TABLE 1-continued

Qualitative detection of 3-hydroxy-2-methyl-4H-1-benzopyran-4-one in rat tissues and its excretion.

| Time after administration | Plasma | Erythrocytes | Liver | Brain | Urine | Faeces |
|---|---|---|---|---|---|---|
| 24 hr | a | a | p(++) | p(++) | p(++) | a |
| 48 hr | a | a | a | a | p(+++) | a |

TABLE 2

Qualitative detection of 3-hydroxy-2-(5-hydroxypentyl)-4H-1-benzopyran-4-one in rat tissues and its excretion.

| Time after administration | Plasma | Erythrocytes | Liver | Brain | Urine | Faeces |
|---|---|---|---|---|---|---|
| 1/4 hr | p(+) | p(+) | a | a | a | a |
| 1/2 hr | p(++) | p(++) | a | a | a | a |
| 1 hr | p(++) | p(+++) | p(+) | a | a | a |
| 4 hr | p(+++) | p(+++) | p(++) | a | a | a |
| 12 hr | a | a | p(++) | p(+) | p(+) | a |
| 24 hr | a | a | p(+++) | p(+) | p(+++) | a |
| 48 hr | a | a | a | a | p(+++) | a | p = present; a = absent.
Plus sign indicates a semi-quantitative score.

What is claimed is:

1. A pharmaceutical composition comprising as the active ingredient at least one compound of formula (I)

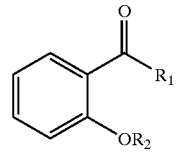

(I)

wherein:

$R_1$ is

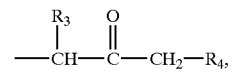

wherein $R_3$ and $R_4$ are selected from the group consisting of H and OH, provided that $R_3$ and $R_4$ are not simultaneously H, and $R_2$ is H; or $R_1$ and $R_2$, taken together are

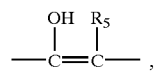

wherein $R_5$ is $(CH_2)_5OH$, or an iron complex thereof.

2. A pharmaceutical composition comprising as the active ingredient an iron complex of the compound of formula (I) as defined in claim 1 wherein $R_5$ is $CH_3$.

3. The pharmaceutical composition according to claim 1, further comprising pharmaceutically acceptable excipients and/or diluents.

4. A compound of formula (I)

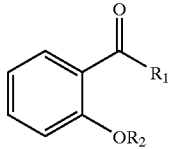
(I)

wherein $R_1$ is

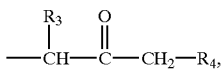

wherein $R_3$ is OH and $R_4$ is H, OH; and $R_2$ is H; or $R_1$ and $R_2$, taken together, are

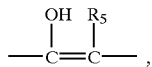

wherein $R_5$ is $(CH_2)_5OH$.

5. The pharmaceutical composition according to claim 2, further comprising pharmaceutically acceptable excipients and/or diluents.

6. A method of treating the conditions associated with an iron overload comprising administering to an individual affected by an iron overload an effective amount of a compound of formula (I)

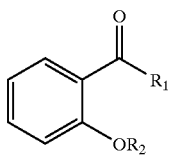
(I)

wherein:

$R_1$ is

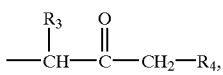

wherein $R_3$ and $R_4$ are selected from the group consisting of H and OH, provided that $R_3$ and $R_4$ are not simultaneously H, and $R_2$ is H; or $R_1$ and $R_2$, taken together, are

wherein $R_5$ is selected from the group consisting of $CH_3$ and $(CH_2)_5OH$.

7. The method according to claim 6, wherein the conditions with which an iron overload is associated comprise hemochromatosis, thalassemia, anemia associated with iron overload and conditions associated with secondary siderosis, neurodegenerative pathologies comprising Parkinson's disease and Alzheimer's disease, ischaemic cardiopathy, inflammatory pathologies comprising arthritis, pyelonephritis and chronic inflammatory diseases of intestine, alterate conditions in the iron metabolism associated with HIV infections, cardiotoxicity due to doxorubicin and anthracyclines, atherosclerosis and senescence.

8. An iron complex of the compound of formula (I)

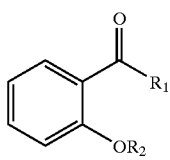
(I)

wherein:

$R_1$ is

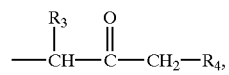

wherein $R_3$ and $R_4$ are selected from the group consisting of H and OH, provided that $R_3$ and $R_4$ are not simultaneously H, and $R_2$ is H; or $R_1$ and $R_2$ taken together are

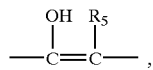

wherein $R_5$ is selected from the group consisting of $(CH_2)_5OH$ and $CH_3$.

9. The iron complex according to claim 8, wherein the molar ratio of formula (I) to iron is 2:1.

10. The iron complex according to claim 8, wherein iron is Fe (III).

11. A method of treating the conditions which are associated with a lack of iron comprising administering an effective amount of iron complexes as defined in claim 8.

12. The method according to claim 11, wherein the conditions with which a lack of iron is associated comprise sideropenic anemia in the acute phase and chronic sideropenic anemia.

* * * * *